United States Patent [19]

Schaarschmidt et al.

[11] Patent Number: 4,662,231

[45] Date of Patent: May 5, 1987

[54] SAMPLE TAKING DEVICE

[75] Inventors: Ulrich Schaarschmidt, Stutensee; Rolf Berg, Bruchsal, both of Fed. Rep. of Germany

[73] Assignee: Wiederaufarbeitungsanlage Karlsruhe Betriebs-Gesellschaft mbH, Eggenstein-Leopoldshafen, Fed. Rep. of Germany

[21] Appl. No.: 672,180

[22] Filed: Nov. 15, 1984

[30] Foreign Application Priority Data

Nov. 24, 1983 [DE] Fed. Rep. of Germany ....... 3342470

[51] Int. Cl.$^4$ .......................... G01N 1/28; G01N 1/34; G01N 1/14
[52] U.S. Cl. .................................. 73/863; 73/864.23; 73/864.31; 73/864; 141/130; 141/329
[58] Field of Search ................ 73/863, 864.23, 864.74, 73/864.51, 864, 864.24, 864.25, 864.31, 864.91; 141/130, 329

[56] References Cited

U.S. PATENT DOCUMENTS

| | | | |
|---|---|---|---|
| 3,383,923 | 5/1968 | Conche et al. | 73/864.31 X |
| 4,041,994 | 8/1977 | Horwitz et al. | 141/329 X |
| 4,160,382 | 7/1979 | Finsterwalder et al. | |
| 4,377,880 | 3/1983 | Jackson et al. | 73/864.24 X |
| 4,467,708 | 8/1984 | Twiford et al. | 141/329 X |
| 4,476,733 | 10/1984 | Chlosta et al. | 73/863 X |
| 4,483,205 | 11/1984 | Bellaiche et al. | 73/864.31 X |
| 4,512,203 | 4/1985 | Calame-Lonjean et al. | 73/864.31 X |
| 4,516,436 | 5/1985 | Conche et al. | 73/864.31 X |

FOREIGN PATENT DOCUMENTS

| | | | |
|---|---|---|---|
| 2617594 | 11/1976 | Fed. Rep. of Germany | 73/864.23 |
| 2642065 | 6/1981 | Fed. Rep. of Germany | |
| 712385 | 8/1966 | Italy | 73/864.23 |
| 463026 | 3/1975 | U.S.S.R. | 73/864.31 |

Primary Examiner—Stewart J. Levy
Assistant Examiner—Tom Noland
Attorney, Agent, or Firm—Spencer & Frank

[57] ABSTRACT

An apparatus for taking a sample of a toxic and/or radioactive substance by introducing such substance into a sample vessel. The apparatus includes a rotatable cylinder containing a recess for receiving a sample vessel. A drive shaft is connected to the cylinder for imparting rotary and axial movements to the cylinder for moving the recess of the cylinder between first and second positions. A needle head filling system is arranged above the cylinder at the first position for filling a sample vessel with toxic and/or radioactive substances. The cylinder is lifted by the shaft for engagement with the needle head filling system when being filled and lowered by the shaft after being filled. An inlet and outlet conduit is provided having one end for receiving from and discharging into the recess of the cylinder a sample vessel, the one end being located above the cylinder at the second position. A stripper is located between the cylinder and the needle head filling system for disengaging the sample vessel from the needle head filling system when the cylinder is lowered by the shaft after being filled.

14 Claims, 1 Drawing Figure

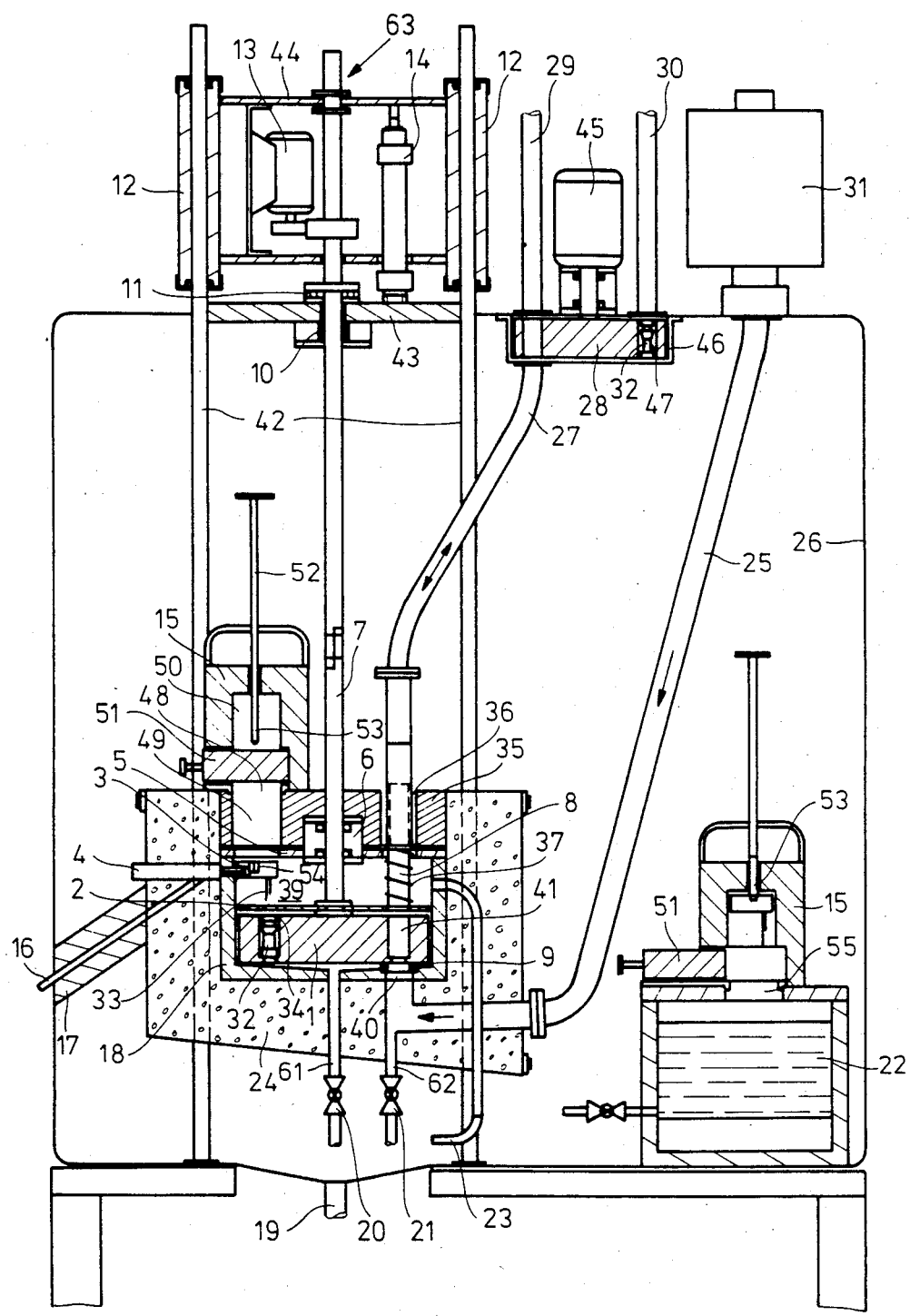

SAMPLE TAKING DEVICE

BACKGROUND OF THE INVENTION

The present invention relates to a sample taking device for toxic and/or radioactive substances with the device performing turning and lifting movements and being provided with a needle head filling system for at least one sample vessel. The device can be moved to the needle head filling system and to an inlet and outlet conduit by means of the turning and lifting movement performed on a rotatable cylinder.

Such a sample taking device is known from German Pat. No. 2,642,065 and corresponding U.S. Pat. No. 4,160,382. However, that device has considerable drawbacks. For example, the regions of the needle heads and of the rotational transport of the sample vessels have dimensions which make shielding in the highly active region difficult. The arrangement of the needles in an upward orientation, i.e. placement of the sample vessels onto the needles from the top to the bottom, requires long needle lengths and easily causes the needles to bend. Moreover, the sample vessels can be filled with sample solution only to a maximum of 75% of their volume. Additionally, the mechanism and structure of the lifting drive is excessively complicated, requiring three lifting cylinders, which are massive structures, and the needle heads cannot be exchanged under conditions of high activity shielding.

SUMMARY OF THE INVENTION

It is therefore an object of the present invention to provide a sample taking device of the above type which permits, from a mechanical and engineering point of view, single or multiple sample taking with good radiation protection and with the possibility for good decontamination of parts charged with radioactivity or toxicity.

The above and other objects are accomplished by the invention wherein an apparatus is provided for taking a sample of at least one of toxic and radioactive substance by introducing such substance into a sample vessel, the apparatus including a rotatable cylinder, the cylinder containing a recess for receiving a sample vessel; a drive shaft connected to the cylinder, the drive shaft being mounted for imparting rotary and axial movements to the cylinder for moving the recess of the cylinder between first and second positions; needle head filling means arranged above the cylinder and at the first position for filling a sample vessel with at least one of the toxic and radioactive substances, the cylinder being lifted by the shaft for engagement with the needle head filling means when being filled and lowered by the shaft after being filled; an inlet and outlet conduit having one end for receiving from and discharging into the recess of the cylinder a sample vessel, the one end being located above the cylinder at the second position; and stripper means located between the cylinder and the needle head filling means for disengaging the sample vessel from the needle head filling means when the cylinder is lowered by the shaft after being filled.

One of the particular advantages provided by the present invention is that the sample vessel transporting elements are driven vertically and rotationally by means of a circular shaft to which the drive motor mechanism is connected, the latter being arranged above the needle head region. Connected with this is an arrangement of the needle heads, i.e. the needle tips, in a downward orientation. The sample vessel to be filled is placed onto the needles from below the needles and moved upward. Another advantage is that the vertical and rotational mechanisms for transporting the sample vessels from the magazine to the filling station and to the pneumatic tube conveyor station is comprised of only three structural elements the rotary turret for entering sample bottles into the sample taking device, the rotary cylinder or turret, and the stripper plate for taking samples. The pneumatic tube conveyor is sealed at its discharge end in the sample taking device head simply by means of structural members comprised of a helical spring and a sleeve.

In a further aspect of the invention a decontamination unit operating with ultrasound for the sample taker components is integrated into the sample taking containment housing. According to another aspect of the invention, the sample taking cylinder region can be advantageously decontaminated by rinsing. In another aspect of the invention provision is also made for rinsing the sample taking conduits. Further, screens can be incorporated for retaining solid decontaminates.

The sample taking device of the invention is thus simplified relative to known sample taking devices. The device of the present invention permits easy filling of the sample vessels with sample medium. Because of the fact that it is possible to rinse the sample taking conduits, which may retain solids, the sample taking device is equipped with preventive mechanisms for preventing and eliminating operational interruptions, such as, for example, clogging during the taking of samples of inhomogeneous liquids. Additionally, the sample taking device of the invention, due to its minimized structural size, has the optimum geometry for radiation protective shielding in the needle head region.

BRIEF DESCRIPTION OF THE DRAWINGS

The sole FIGURE of the drawings is a vertical sectional view of a sample taking device according to the invention.

DESCRIPTION OF THE PREFERRED EMBODIMENT

Referring to the FIGURE, a rotatable cylinder 1 (also referred to as a revolving head) is provided for holding a sample vessel 32 in a recess 41 and for transporting the sample vessel from a charging position below the open end of an inlet and outlet (transporting) conduit 27 to a needle head filling system 3 of known construction which include two downwardly oriented hollow needles 33. A horizontal media intake and discharge conduit 16 communicates with needle head filling system 3. Although cylinder 1 is described and illustrated herein as having only one recess 41, it should be apparent that a plurality of such recesses may be provided in cylinder 1 for holding and transporting a plurality of sample vessels.

Rotatable cylinder 1 is rotated into the various positions and at the same time raised and lowered by means of a drive shaft 7. The stroke of this movement is arranged so that, during filling, the sample vessel 32 can be raised from below and onto the hollow needles 33. For this purpose, needles 33, sample vessel 32 and the recess 41 in cylinder 1 for accommodating the sample vessel 32, are each oriented parallel to the axis of drive shaft 7.

A stripper 2, secured against rotation, is likewise disposed on drive shaft 7, above cylinder 1, so as to be carried along during the lifting movement, but not during the rotational movement of cylinder 1. Stripper 2 is preferably a plate provided with openings 34 which are able to correspond with the needles 33 in the region of the needle head filling system 3. Openings 34 permit the passage of the needles 33 for filling the sample vessel 32. Further, stripper 2 takes care that the sample vessel 32 is removed from needles 33 when the filling process is completed and cylinder 1 is lowered back to its starting position.

Cylinder 1, stripper 2 and the needle head filling system 3 are disposed in a housing 18 comprised of a sheet metal box filled with shielding material, preferably lead shots. The media intake and discharge conduit 16 is likewise shielded, preferably with lead wool 17, and passes through the wall of housing 18 so that a connection to two corresponding conduits in the needle head filling system 3 and to the hollow needles 33 is established. The needle head filling system 3 is positioned and tightly held to the wall of housing 18 by means of a fastening screw 4. The fastening screw 4 is made of massive stainless steel and has a threaded end which is screwed into a corresponding bore in the needle head filling system 3.

Sample taking device housing 18 is further provided with a shielding cover 35 through which passes drive shaft 7 which is fastened to housing 18 by means of a bearing 6. Moreover, inlet and outlet conduit 27 passes through an opening 36 in cover 35 and terminates over the surface of cylinder 1. The lower end of conduit 27 is designed to be telescoping in that a sleeve 8 is movable in conduit 27 so that, during the lifting movement of cylinder 1, the length of conduit 27 can be varied. A spring 37 which presses sleeve 8 onto cylinder 1 ensures that sleeve 8 is lowered to its starting position. Spring 37 and bearing 6 are held by cover 35.

At the bottom of sample taking device housing 18, whose interior 39 has the shape of a funnel, there is provided a de-watering conduit 61 with valve 20 and a de-watering conduit 62 with valve 21. Laterally, a pneumatic tube conveyor air intake conduit 25 leads into shielding housing 24 so as to end in an opening 40 at the bottom of the interior 39 of the sample taking device housing 18, precisely below the open end of sleeve 8 so that, in the illustrated charging position of cylinder 1, a recess 41 for accommodating a further sample vessel 32 is flush with both the open end of sleeve 8 and opening 40. Conduit 25 is sealed against cylinder 1 about opening 40 by means of a seal 9 in order to prevent escape of the pneumatic drive medium.

Sample taking device housing 18 is secured to a rod assembly 42 via the material of shielding housing 24. This rod assembly 42 also serves to slidably mount the driving mechanism 63 which imparts rotary and lifting movements to drive shaft 7. The driving mechanism 63 comprises at least one lifting cylinder 14 for the vertical (axial) stroke and a motor 13 for the rotational drive. Lifting cylinder 14 acts against a stationary plate 43 and raises or lowers shaft 7 via a plate 44 to which shaft 7 is fastened and which serves as the pressure surface for lifting cylinder 14. Two vertical guides 12 at rod assembly 42 are attached to plate 44 and are guided over rod assembly 42. A bearing 11 at plate 43 holds drive shaft 7 in position with respect to a counterbearing 6 in cover 35.

Driving mechanism 63 is seated outside a glovebox 26 which accommodates the sample taking device. Rod assembly 42 passes through the walls of glovebox 26 in a sealed manner. Plate 43 forms part of the wall of glovebox 26. Drive shaft 7 is sealed against the interior of box 26 by means of a seal 10.

Transporting conduit 27 is connected between sleeve 8 and a transfer device in the form of a turret 28 for supplying sample vessels 32 from an empty vessel magazine (not shown) to cylinder 1 for subsequent filling and for transporting the sample vessels after filling to a pneumatic tube conveyor conduit 29. Turret 28 is disposed at the underside of the wall of box 26. Turret 28 is disposed in a sealed, small housing 46 and is rotated by means of a rotary drive motor 45 so that in one position an empty sample vessel from a magazine tube 30 can be supplied to a recess 47 of turret 28 and in a second position, with recess 47 above transporting tube 27, a continuous connection exists from transporting tube 27 to pneumatic tube conveyor conduit 29 outside of box 26. When this contineous connection between transporting tube 27 and pneumatic tube conveyor conduit 29 exists through recess 47, the empty vessel will fall into recess 41; when sampling has taken place the filled vessel can pass through transporting tube 27 through recess 47 and further through pneumatic tube conveyor conduit 29 to its final destination. Instead of turret 28, a pusher device may also be employed which is operated or controlled, respectively, by carriers on drive shaft 7 or the like.

Cover 35 of the sample taking device is provided with a recess 48 above needle head filling system 3. The recess 48 is large enough to permit needle head filling system 3 with needles 33 to be withdrawn in an upward direction. A plug corresponding to the recess 48 is placed into and seals this recess.

The entire cover 35 need not be airtight. It must only fulfill the requirement of shielding against radiation. A shield of 50 mm stainless steel is recommended for head cover 35. Lead is not suitable as shielding material in the acid vapor atmosphere which escapes from needle head filling system 3 into the interior.

In order to exchange the radiation charged needle head filling system 3, a shielded transparting vessel 15 is placed onto opening 48 from which the plug has been removed and needle head filling system 3 is pulled into vessel 15. In its interior, shielded transporting vessel 15 has a cavity 50 sized to hold needle filling system 3 with needles 33.

A round stainless steel rod 52 is integrated into the transporting vessel 15 and is positioned precisely above a fastening screw 4 which secures the needle head filling system 3. The steel rod has a threaded end 53 which is screwed into a corresponding bore 54 of the needle head filling system 3 so that said system 3 can be pulled into shielding cavity 50 after having loosened fastening screw 4.

Needle head filling system 3 is brought over a discharging position 55 of an ultrasound bath 22 disposed in glovebox 26. There, after opening slide 51 and unscrewing threaded end 53, the needle head filling system 3 is discharged into ultrasound bath 22. In ultrasound bath 22, the needle head filling system 3 is decontaminated down to doses that can be handled without shielding. The foregoing exchange and decontamination procedures can be performed manually via glovebox 26 is a well known manner.

The high activity sample taking device and glovebox 26 are connected to liquid water conduit 19.

Inner chamber 39 and cylinder 1 disposed therein can be decontaminated. The decontamination liquid is discharged through conduits 61 and 62 equipped with valves 20 and 21, respectively. An overflow conduit 23 is brought through the side wall of housing 18 and through shielding housing 24 to the bottom of glovebox 26.

The housing 24 can be filled with an appropriate shielding material such as lead shots or concentrated salt solutions. The pusher 28 is a rectangular stainless steel block with a bore 47 contained in a housing 29. By aid of a pneumatic cylinder 27 the bore can be positioned under the sample vessel magazine 30 in which case the sampler is sealed off from the pneumatic tube conduit 29, or under the pneumatic tube conduit 29 in which case the sample vessel 32 can fall into the recess 42 or be transported away after sampling through the pneumatic tube conduit 29.

It will be understood that the above description of the present invention is susceptible to various modifications, changes and adaptations, and the same are intended to be comprehended within the meaning and range of equivalents of the appended claims.

What is claimed is:

1. An apparatus for taking a sample of at least one of a toxic and radioactive substance by introducing such substance into a sample vessel, comprising:

a rotatable cylinder, said cylinder containing a recess for receiving a sample vessel;

a drive shaft connected to said cylinder, said drive shaft being mounted for imparting rotary and axial movements to said cylinder for moving the recess of said cylinder between first and second positions;

needle head filling means arranged above said cylinder and at the first position for filling a sample vessel with at least one of the toxic and radioactive substances, said cylinder being lifted by said shaft for engagement with said needle head filling means when being filled and lowered by said shaft after being filled;

an inlet and outlet conduit having one end for receiving from and discharging into the recess of said cylinder a sample vessel, said one end being located above said cylinder at the second position; and stripper means located between said cylinder and said needle head filling means for disengaging the sample vessel from said needle head filling means when said cylinder is lowered by said shaft after being filled.

2. An apparatus as defined in claim 1, wherein said needle head filling means includes at least one needle for filling the sample vessel and said stripper means comprises a disc which is mounted on said drive shaft and which includes one opening for the passage of said inlet and outlet conduit and another opening for the passage of said at least one needle.

3. An apparatus as defined in claim 1, wherein said inlet and outlet conduit has a second end which is remote from said cylinder with respect to said one end, and further including a magazine tube for providing an empty sample vessel from a store of empty sample vessels, a transfer means connected to said magazine tube and located at said second end for receiving an empty sample vessel from said magazine tube, inserting the empty sample vessel into said inlet and outlet conduit, and for closing and opening, respectively, the second end of said inlet and outlet conduit.

4. An apparatus as defined in claim 3, wherein said transfer means includes one of a rotary cylinder and a pusher.

5. An apparatus as defined in claim 3, and further including a housing having a wall enclosing said cylinder, stripper means and needle head filling means; a box enclosing said housing; a first drive means disposed at said drive shaft for imparting rotary and axial movement to said drive shaft and a second drive means connected to said transfer means for driving said transfer means, said second drive means being disposed outside said box.

6. An apparatus as defined in claim 1, wherein the one end of said inlet and outlet conduit includes a telescoping means for changing the length of said inlet and outlet conduit at said one end during axial movements of said cylinder.

7. An apparatus as defined in claim 1, and further including a rod assembly and drive means supported by said rod assembly and connected to said drive shaft, said drive means including a lifting cylinder for providing axial movement to said drive shaft and a rotary drive for providing rotary movement to said drive shaft, said drive means being vertically guided along said rod assembly and secured against twisting by said rod assembly.

8. An apparatus as defined in claim 1, and further including a housing having a wall enclosing said cylinder, stripper means and said needle head filling means, said drive shaft and said inlet and outlet conduit being brought through the wall of said housing.

9. An apparatus as defined in claim 8, and further including a rod assembly, said housing being fastened to said rod assembly.

10. An apparatus as defined in claim 8, and further including an inlet tube for supplying a pneumatic tube drive medium to said inlet and outlet conduit, said inlet tube being brought through the wall of said housing, said inlet tube terminating underneath said cylinder in a position opposite the one end of said inlet and outlet conduit.

11. An apparatus as defined in claim 8, wherein said drive shaft is mounted in said housing.

12. An apparatus as defined in claim 8, wherein the walls of said housing are constructed as a shield against radioactivity.

13. An apparatus as defined in claim 8, wherein said housing has an upper side and a closable opening passing through said upper side, said closable opening being disposed above said needle head filling means, with said needle head filling means being removable from said housing through said closable opening.

14. An apparatus as defined in claim 8, wherein said housing as an interior and includes an outlet at the bottom of said housing for emptying material from the interior of said housing.

* * * * *